(12) United States Patent
Sevenster et al.

(10) Patent No.: US 10,235,360 B2
(45) Date of Patent: Mar. 19, 2019

(54) GENERATION OF PICTORIAL REPORTING DIAGRAMS OF LESIONS IN ANATOMICAL STRUCTURES

(75) Inventors: Merlijn Sevenster, Eindhoven (NL); Yuechen Qian, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 13/997,277

(22) PCT Filed: Dec. 16, 2011

(86) PCT No.: PCT/IB2011/055737
§ 371 (c)(1),
(2), (4) Date: Jun. 24, 2013

(87) PCT Pub. No.: WO2012/085795
PCT Pub. Date: Jun. 28, 2012

(65) Prior Publication Data
US 2013/0275124 A1    Oct. 17, 2013

Related U.S. Application Data

(60) Provisional application No. 61/426,545, filed on Dec. 23, 2010.

(51) Int. Cl.
*G06F 17/27* (2006.01)
*G06F 17/28* (2006.01)
(Continued)

(52) U.S. Cl.
CPC ............ *G06F 17/28* (2013.01); *G06F 17/277* (2013.01); *G06F 17/2785* (2013.01); *G16H 15/00* (2018.01); *G16H 80/00* (2018.01)

(58) Field of Classification Search
CPC ...... G06F 17/27; G06F 17/20; G06F 17/2705; G06F 17/271; G06F 17/2715;
(Continued)

(56) References Cited

U.S. PATENT DOCUMENTS 6,021,404 A * 2/2000 Moukheibir .................... 706/46
6,161,084 A   12/2000 Messerly et al.
(Continued)

FOREIGN PATENT DOCUMENTS

EP     2169577 A1   3/2010
JP   2006059063 A   3/2006
(Continued)

OTHER PUBLICATIONS

Golland, P. et al. "Anatomy Browser: A framework for integration of medical information". Lecture Notes in Computer Science 1486, Medical Image Computing and Computer Assisted intervention, MICCAI'98, First International Conference Cambridge, MA (1998), Proceedings. pp. 728-729, Section 3.6 and 4.0.
(Continued)

*Primary Examiner* — Lamont M Spooner

(57) ABSTRACT

The invention relates to a system (SYS) for automatically extracting a location of an abnormality with respect to an anatomical structure from a report, the system comprising a tokenizer (U10) for tokenizing the report or a part of it, thereby producing a plurality of tokens, and an analyzer (U20) for identifying a semantic structure comprising identified tokens of the plurality of tokens, describing the location of the abnormality with respect to the anatomical structure. Optionally, the system further comprises a mapper (U30) for annotating a diagram representing the anatomical structure, based on the identified semantic structure describing the location of the abnormality with respect to the anatomical structure. Using the system, the location of the
(Continued)

abnormality with respect to the anatomical structure can be extracted from each report of the plurality of reports produced over the period of time. The extracted locations may be used by a clinician for diagnostic purposes.

20 Claims, 5 Drawing Sheets

(51) Int. Cl.
*G16H 80/00* (2018.01)
*G16H 15/00* (2018.01)

(58) Field of Classification Search
CPC .. G06F 17/272; G06F 17/2725; G06F 17/273; G06F 17/2735; G06F 17/274; G06F 17/2745; G06F 17/275; G06F 17/2755; G06F 17/276; G06F 17/2765; G06F 17/277; G06F 17/2775
USPC .......................... 704/1, 9, 10; 707/706–708
See application file for complete search history.

(56) References Cited

U.S. PATENT DOCUMENTS

| | | | |
|---|---|---|---|
| 6,182,029 B1 | 1/2001 | Friedman | |
| 7,738,684 B2 | 6/2010 | Kariathungal et al. | |
| 7,818,177 B1 | 10/2010 | Bangalore et al. | |
| 7,822,598 B2* | 10/2010 | Carus et al. | 704/9 |
| 2003/0099384 A1* | 5/2003 | Zeng | G06T 7/0012 382/128 |
| 2004/0151358 A1* | 8/2004 | Yanagita et al. | 382/132 |
| 2005/0108001 A1* | 5/2005 | Aarskog | 704/10 |
| 2006/0248349 A1* | 11/2006 | Rathjen | G06F 19/26 713/186 |
| 2006/0274928 A1* | 12/2006 | Collins et al. | 382/132 |
| 2007/0064987 A1* | 3/2007 | Esham et al. | 382/128 |
| 2007/0237377 A1 | 10/2007 | Oosawa | |
| 2008/0103828 A1 | 5/2008 | Squilla et al. | |
| 2009/0287663 A1* | 11/2009 | Takeuchi | 707/3 |
| 2009/0300550 A1* | 12/2009 | Ruland | 715/841 |
| 2009/0310836 A1* | 12/2009 | Krishnan et al. | 382/128 |
| 2010/0114597 A1 | 5/2010 | Shreiber et al. | |
| 2010/0284587 A1* | 11/2010 | Malek | A61B 5/02014 382/128 |
| 2011/0137132 A1* | 6/2011 | Gustafson | 600/300 |
| 2013/0275124 A1 | 10/2013 | Sevenster et al. | |

FOREIGN PATENT DOCUMENTS

| | | |
|---|---|---|
| JP | 2008108078 A | 5/2008 |
| WO | 199819253 A1 | 5/1998 |
| WO | 2010109351 A1 | 9/2010 |

OTHER PUBLICATIONS

Friedman, C. et al "Automated encoding of clinical documents based on natural language processing". Journal of the American Medical Informatics Association. Sep.-Oct. 2004, 11(5), Philadelphia, PA, US. vol. 11, No. 5, pp. 392-402.

Friedman, C. et al "A general natural-language text processor for clinical radiology". Journal of the American Medical Informatics Association. vol. 1, No. 2, Mar./Apr. 1994. pp. 161-174.

Sevenster, M. et al. "Automatically correlating clinical findings and body locations in radiology reports using medLee." Journal of Digital Imaging. Springer-Vertag, Apr. 2012, vol. 25, Issue 2 pp. 240-249.

Friedman, C et al. "Natural language processing in an operational clinical information system". Natural Language Engineering, Cambridge University Press, Cambridge, GB. vol. 1, No. 1 Mar. 7, 1995, pp. 83-108.

Friedman, C. et al. "A conceptual model for clinical radiology reports". Proceedings. Symposium on Computer applications in Medicalcare. US. Oct. 30, 1993. pp. 829-833.

Gschwandtner, T. et al. "Mapface—A graphical editor to support the semantic annotation of medical text". Institute of Software Technology and Interactive Systems, Vienna University of Technology, Vienna, Austria. Proceedings of the Junior Scientist Conference 2008 (JSC'08), pp. 91-91. http://publik.tuwien.ac.at/files/PubDat_168176.pdf.

* cited by examiner

EXAM: IOE US OUTSIDE EXAM, IOE MAM OUTSIDE EXAM, IOE MAM OUTSIDE EXAM, IOE MAM OUTSIDE EXAM

CLINIC INFORMATION: New right breast cancer diagnosis presenting for second opinion. The patient was recalled from screening mammogram for an asymmetric subareolar poorly defined density in the right breast. She underwent ultrasound guided core biopsy with a pathologic result of "Right breast periareolar region, ultrasound guided core biopsy: Invasive ductal carcinoma, grade 2, measuring 1.2 cm in greatest core length." Previous diagnostic workup two-years prior for a mass in the upper outer right breast revealed a cyst.

SUBMITTED IMAGES: Imaging includes bilateral hard copy digital mammographic images and implant displaced views dated 2 weeks prior. Spot magnification views of the retroareolar right breast dated 2 weeks prior, and bilateral post procedure CC and MLO views of the right breast, implant displaced, dated ten days prior. Comparison mammogram dated two-years prior is provided, 25 static ultrasound images of the right breast dated two weeks prior and 30 static ultrasound images from ultrasound guided core biopsy dated 10 days ago.

FINDINGS:
The breast parenchyma is composed of scattered fibroglandular elements, unchanged in pattern and distribution. Bilateral prepectoral silicone implants are in place. Benign calcifications including arterial calcifications are present. No dominant masses, suspicious microcalcifications or areas of architectural distortion are present in the left breast. A 1.2 cm spiculated mass is present in the right periareolar region, slightly lateral and central to the nipple. This persists on spot compression images. No associated microcalcifications are present. A 1.2 cm lobular mass in the superior lateral right breast, anterior-mid depth is again seen. A 1 cm oval mass with obscured margins is seen in the lateral right breast, mid depth, on the CC image only.

Sonographic images labeled "right periareolar / 9 o'clock" demonstrate an isoechoic round nonparallel mass with microlobulated margins measures 1.2 x 0.9 x 0.9 cm. Doppler imaging is not provided. At the 10 o'clock position of the right breast, 2 cm from the nipple, an oval, parallel, mixed echogenicity mass measuring 1.0 x 0.7 x 0.3 cm is present.
This may correspond to the lobular mass in the superior lateral right breast.

Images from ultrasound guided core biopsy demonstrates adequate targeting of the retroareolar mass. Post procedure mammogram demonstrates a clip immediately adjacent to the spiculated mass in the retroareolar right breast.

IMPRESSION:
New breast cancer diagnosis in a 1.2-cm spiculated mass in the retroareolar right breast.
Two additional masses in the right breast, one of which was a cyst per prior imaging report.
However submitted ultrasound demonstrates a mixed echogenicity mass not consistent with a cyst.
Further evaluation of this mass and an additional mass seen only on the CC image is recommended Normal left mammogram.

RECOMMENDATIONS:
1. Bilateral breast MRI for staying.

2. Additional diagnostic workup for both the lobular mass in the superior lateral right breast and the 1 cm oval mass in the lateral right breast, mid depth.

3. Right axiliary ultrasound

FIG. 2

| Identifier | Type | Laterality | Location | Depth |
|---|---|---|---|---|
| 1 | Mass | Right | Periareolar/lateral/central to the nipple | |

☐ IBW Report Viewer for UCMC

File   Settings   Help       Accession Number [    ]   Load From VIB

Current study

24-Oct-2008, US
d742e754fea410b9 ultrasound images from ultrasound guided core biopsy dated 10 days ago.

FINDINGS:
The breast parenchyma is composed of scattered fibroglandular elements, unchanged in pattern and distribution. Bilateral prepectoral silicone implants are in place. Benign calcifications including arterial calcifications are present. No dominant masses, suspicious microcalcifications or areas of architectural distortion are present in the left breast. A 1.2 cm spiculated mass is present in the right periareolar region, slightly lateral and central to the nipple.
This persists on spot compression images. No associated microcalcifications are present.
A 1.2 cm lobular mass in the superior lateral right breast, anterior-mid depth is again seen.
A 1 cm oval mass with obscured margins is seen in the right breast, mid depth,
on the CC image only.

Sonographic images labelled "right periareolar / 9 o'clock" demonstrate an isoechoic round nonparellel mass with microlobulated margins measures 1.2 x 0.9 x 0.9 cm. Doppler imaging is not provided. At the 10 o'clock position of the right breast, 2 cm from the nipple, an oval, parallel, mixed echogenicity mass measuring 1.0 x 0.7 x 0.3 cm is present.
This may correspond to the lobular mass in the superior lateral right breast.

Images from ultrasound guided core biopsy demonstrates adequate targeting of the retroareolar mass. Post procedure mammogram demonstrates a clip immediately adjacent to the spiculated mass in the retroareolar right breast.

IMPRESSION:

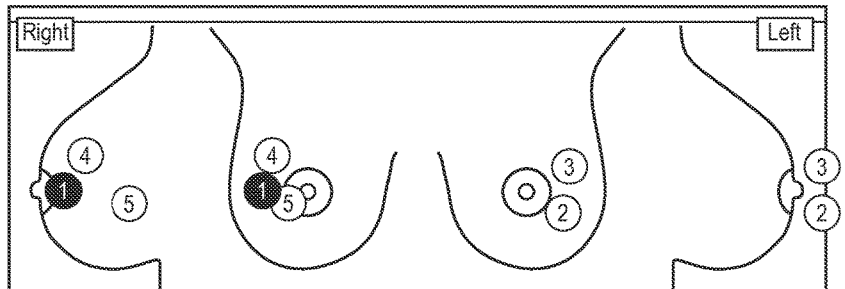

FIG. 3

GENERATION OF PICTORIAL REPORTING DIAGRAMS OF LESIONS IN ANATOMICAL STRUCTURES

FIELD OF THE INVENTION

The invention relates to the generation of pictorial reporting diagrams of lesions in anatomical structures.

BACKGROUND OF THE INVENTION

Radiology plays an important role in the care process. Throughout the care cycle, multiple imaging studies are conducted on each patient. The images are typically acquired with more than one imaging modality, including computed tomography, magnetic resonance tomography, positron emission tomography, ultrasound and x-ray.

For each patient, it is essential to keep track of the development of abnormalities over time. This task becomes even more complex when multiple abnormalities need to be taken into account. Each abnormality must be assessed and possibly related to the corresponding abnormality in a previous study.

The status of each abnormality is described in many reports produced at the time of the study. The reports can be structured or unstructured. To track an abnormality over time one must thus interpret the content of these reports. This is a tedious and time-consuming task, prone to human errors. Erroneously combining different abnormalities in different reports may lead to misdiagnoses.

EP-2169577 A1 by Reuven Schreiber et al., entitled *Method and system for medical imaging reporting*, discloses a system that automatically matches a reporting template of an organ to medical imaging studies, thereby embedding diagnosis and images in it, and presenting the matched template to a radiologist for diagnosis. However, that system does not use the text of the report to determine the location or properties of an organ.

SUMMARY OF THE INVENTION

It would be advantageous to have a system capable of identifying locations of corresponding abnormalities in a plurality of text reports produced over a period of time.

Thus, in an aspect, the invention provides a system for automatically extracting a location of an abnormality with respect to an anatomical structure from a report, the system comprising:
  a tokenizer for tokenizing the report or a part of it, thereby producing a plurality of tokens; and
  an analyzer for identifying a semantic structure comprising identified tokens of the plurality of tokens, describing the location of the abnormality with respect to the anatomical structure.

Using the system, the location of the abnormality with respect to the anatomical structure can be extracted from each report of the plurality of reports produced over the period of time. The extracted locations may be used by a clinician for diagnostic purposes.

In an embodiment of the system, identifying the semantic structure involves comparing conceptual tokens of the plurality of tokens to concepts of a plurality of concepts in order to determine the identified tokens. The concepts of the plurality of concepts may include concepts describing possible anatomical structures, their abnormalities, and locations of an abnormality with respect to an anatomical structure. By determining a conceptual token which is identical to a concept describing a possible location of the abnormality with respect to the anatomical structure, the system may be adapted for choosing the possible location of the abnormality with respect to the anatomical structure as the identified location of the abnormality with respect to the anatomical structure.

In an embodiment of the system, comparing conceptual tokens of the plurality of tokens to concepts of a plurality of concepts involves computing a conceptual similarity between the conceptual tokens and the concepts. The concepts of the plurality of concepts may include concepts describing possible anatomical structures, their abnormalities, and locations of an abnormality with respect to an anatomical structure. By determining a conceptual token which is very similar to a concept describing a possible location of the abnormality with respect to the anatomical structure, the system may be adapted for choosing the possible location of the abnormality with respect to the anatomical structure as the identified location of the abnormality with respect to the anatomical structure.

In an embodiment of the system, identifying the semantic structure further involves comparing relational tokens, describing relations between/among the conceptual tokens, to concept relations between/among the concepts of the plurality of concepts, in order to determine relations between/among the identified conceptual tokens. The concepts of the plurality of concepts and concept relations between/among the concepts of the plurality of concepts form an ontology. By including a comparison between relational tokens and concept relations along with the comparison between the conceptual tokens and concepts, the identified location of the abnormality with respect to the anatomical structure is described in more detail by the semantic structure, and thus the identification is more precise.

In an embodiment of the system, comparing the relational tokens to the concept relations between/among the concepts of the plurality of concepts involves computing a relational similarity between the relational tokens and the concept relations.

In an embodiment, the system is further adapted for indicating the location of the abnormality with respect to the anatomical structure on a diagram representing the anatomical structure, the system further comprising a mapper for annotating the diagram representing the anatomical structure, based on the identified semantic structure describing the location of the abnormality with respect to the anatomical structure. A graphical visualization of the location of the abnormality with respect to the anatomical structure on a diagram representing the anatomical structure is easy to comprehend for the clinician and improves the workflow relating to the abnormality investigation and diagnosis.

In an embodiment, the system further comprises an extractor for extracting additional information about the identified abnormality, based on the identified semantic structure, the additional information comprising, for example, the size or palpability of the abnormality. The additional information may be structured by the extractor. Alternatively, the additional information may comprise a pointer to a text from the report for highlighting on a display.

In an embodiment of the system, the anatomical structure is the breast or axilla. Early detection of abnormalities in women's breasts and axillae is an important aspect of women's health programs.

In a further aspect, the invention provides a workstation comprising the system of the invention.

In a further aspect, a method is provided of automatically extracting a location of an abnormality with respect to an anatomical structure from a report, the method comprising:
a tokenizing step for tokenizing the report or a part of it, thereby producing a plurality of tokens; and
an analyzing step for identifying a semantic structure comprising identified tokens of the plurality of tokens, describing the location of the abnormality.

In an implementation of the method, identifying the semantic structure involves comparing conceptual tokens of the plurality of tokens to concepts of a plurality of concepts in order to determine the identified tokens.

In an implementation of the method, identifying the semantic structure further involves comparing relational tokens, describing relations between/among the conceptual tokens, to concept relations between/among the concepts of the plurality of concepts, in order to determine relations between/among the identified conceptual tokens.

In an implementation, the method is further adapted for indicating the location of the abnormality with respect to the anatomical structure on a diagram representing the anatomical structure, the method further comprising a mapping step for annotating the diagram representing the anatomical structure, based on the identified semantic structure describing the location of the abnormality with respect to the anatomical structure.

In an implementation, the method further comprises an extracting step for extracting additional information about the identified abnormality, based on the identified semantic structure, the additional information comprising, for example, the abnormality size or palpability.

In a further aspect, the invention provides a computer program product to be loaded by a computer arrangement, the computer program product comprising instructions for automatically extracting a location of an abnormality with respect to an anatomical structure from a report, the computer arrangement comprising a processing unit and a memory, the computer program product, after being loaded, providing said processing unit with the capability to carry out steps of the method of the invention.

It will be appreciated by those skilled in the art that two or more of the above-mentioned embodiments, implementations, and/or aspects of the invention may be combined in any way deemed useful.

Modifications and variations of the system, of the workstation, of the image acquisition apparatus, of the method, and/or of the computer program product, which correspond to the described modifications and variations of the system or of the method, can be carried out by a person skilled in the art on the basis of the description.

The invention is defined in the independent claims. Advantageous embodiments are defined in the dependent claims.

BRIEF DESCRIPTION OF THE DRAWINGS

These and other aspects of the invention are apparent from and will be elucidated by means of implementations and embodiments described hereinafter and with reference to the accompanying drawings, in which:

FIG. 2 shows an exemplary unstructured report;

FIG. 3 illustrates an example of indicating the location of a lesion on the breast diagram and the additional information in a structured form and in an unstructured form, as highlighted text in the exemplary unstructured report;

Identical reference numerals are used to denote similar parts throughout the Figures.

DETAILED DESCRIPTION OF EMBODIMENTS

Figure 1:
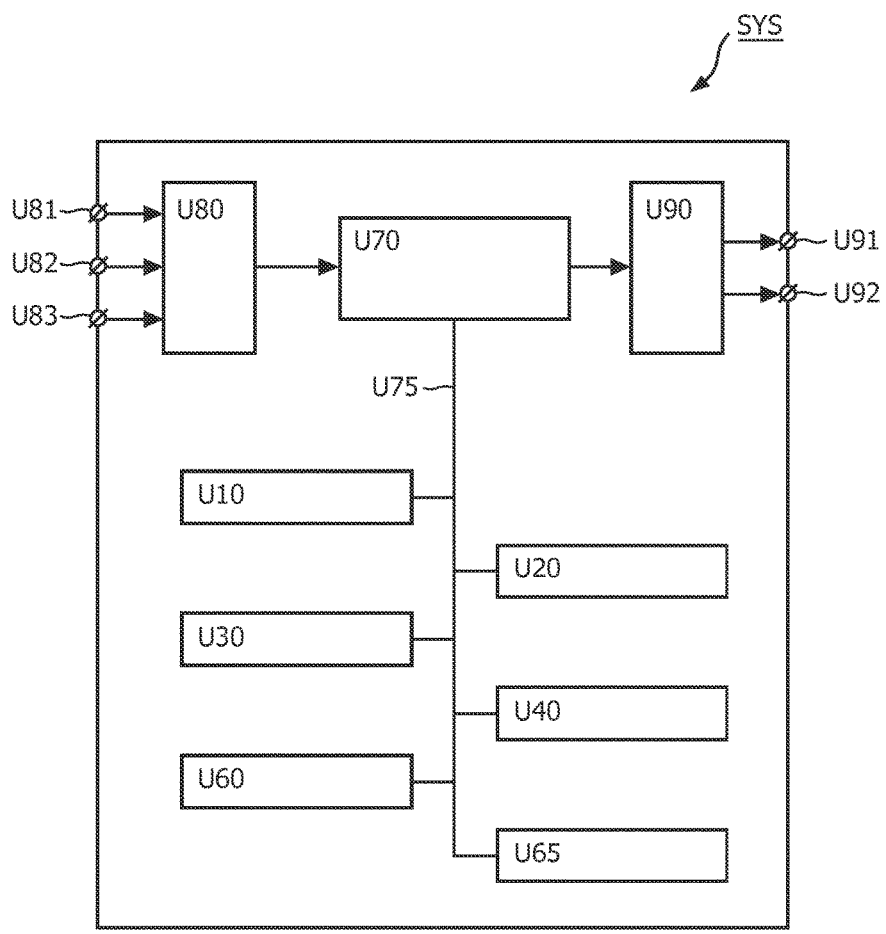
FIG. 1 shows a block diagram of an exemplary embodiment of the system.

FIG. 1 schematically shows a block diagram of an exemplary embodiment of the system SYS for automatically extracting a location of an abnormality with respect to an anatomical structure from a report, the system comprising:
a tokenizer U10 for tokenizing the report or a part of it, thereby producing a plurality of tokens; and
an analyzer U20 for identifying a semantic structure comprising identified tokens of the plurality of tokens, describing the location of the abnormality with respect to the anatomical structure.

The exemplary embodiment of the system SYS further comprises:
a mapper U30 for annotating a diagram representing the anatomical structure, based on the identified semantic structure describing the location of the abnormality with respect to the anatomical structure;
an extractor U40 for extracting additional information about the identified abnormality, based on the identified semantic structure, the additional information comprising, for example, the size or palpability of the abnormality;
a control unit U60 for controlling the work of the system SYS;
a user interface U65 for communication between the user and the system SYS; and
a memory unit U70 for storing data.

In an embodiment of the system SYS, there are three input connectors U81, U82 and U83 for the incoming data. The first input connector U81 is arranged to receive data coming in from a data storage means such as, but not limited to, a hard disk, a magnetic tape, a flash memory, an optical disk, or RIS/PACS systems. The second input connector U82 is arranged to receive data coming in from a user input device such as, but not limited to, a mouse or a touch screen. The third input connector U83 is arranged to receive data coming in from a user input device such as a keyboard. The input connectors U81, U82 and U83 are connected to an input control unit U80.

In an embodiment of the system SYS, there are two output connectors U91 and U92 for the outgoing data. The first output connector U91 is arranged to output the data to a data storage means such as a hard disk, a magnetic tape, a flash memory, or an optical disk, or RIS/PACS systems. The second output connector U92 is arranged to output the data to a display device. The output connectors U91 and U92 receive the respective data via an output control unit U90.

A person skilled in the art will understand that there are many ways to connect input devices to the input connectors U81, U82 and U83 and the output devices to the output connectors U91 and U92 of the system SYS. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment, the system SYS comprises a memory unit U70. The system SYS is arranged to receive input data from external devices via any of the input connectors U81, U82, and U83 and to store the received input data in the memory unit U70. Loading the input data into the memory unit U70 allows quick access to relevant data portions by the units of the system SYS. The input data comprises the report. The memory unit U70 may be implemented by devices such as, but not limited to, a register file of a CPU, a cache memory, a Random Access Memory (RAM) chip, a Read Only Memory (ROM) chip, and/or a hard disk drive and a hard disk. The memory unit U70 may be further arranged to store the output data. The output data comprises the locations of abnormalities and additional information about the abnormalities. The memory unit U70 may be also arranged to receive data from and/or deliver data to the units of the system SYS comprising the tokenizer U10, the analyzer U20, the mapper U30, the extractor U40, the control unit U60, and the user interface U65, via a memory bus U75. The memory unit U70 is further arranged to make the output data available to external devices via any of the output connectors U91 and U92. Storing data from the units of the system SYS in the memory unit U70 may advantageously improve the performance of the units of the system SYS as well as the rate of transfer of the output data from the units of the system SYS to external devices.

In an embodiment, the system SYS comprises a control unit U60 for controlling the system SYS. The control unit U60 may be arranged to receive control data from and provide control data to the units of the system SYS. For example, after tokenizing the report or a part of it, thereby producing a plurality of tokens, the tokenizer U10 may be arranged to provide control data "the report is tokenized" to the control unit U60, and the control unit U60 may be arranged to provide control data "identify a semantic structure describing the location of the abnormality with respect to the anatomical structure", to the analyzer U20. Alternatively, control functions may be implemented in other units of the system SYS.

In an embodiment of the system SYS, the system SYS comprises a user interface U65 for enabling communication between a user and the system SYS. The user interface U65 may be arranged to receive a user input comprising the name of the file comprising the report. Optionally, the user interface may receive a user input for determining the type of abnormality and the anatomical structure. The user interface may be further arranged to display the annotated diagram representing the anatomical structure and showing the location of the abnormality with respect to the anatomical structure. A person skilled in the art will understand that more functions may be advantageously implemented in the user interface U65 of the system SYS.

The aspects, embodiments and implementations of the invention are described with reference to an unstructured breast cancer report comprising a description of a mammographic image. The anatomic structure is the left and right breast of a woman. The abnormality is a tumor in any one of the two breasts. A person skilled in the art will understand that other uses of the invention are also possible and that the scope of the claims should not be construed as being limited to said report by the exemplary application of the invention.

In her/his workflow, a clinician, i.e., in the present case, a care professional trained to analyze a mammographic exam, needs to extract the locations of the abnormalities from an existing report, because abnormalities found in the report need to be re-examined. FIG. 2 shows an exemplary unstructured report of a mammographic exam of the breasts.

The system SYS of the invention is capable of providing the clinician with the needed locations of abnormalities. This can be implemented using a natural language processing engine which is arranged for analyzing the content of the report and extracting the required information. First, the report is tokenized by the tokenizer U10, which is adapted for producing a plurality of tokens, e.g., words or terms, comprised in the report. Using a vocabulary which is constructed by the user, or which is based on a standard vocabulary pertaining to breast cancer, such as the SNOMED CT or BI-RADS vocabularies, the analyzer U20 is adapted for analyzing the plurality of tokens to identify conceptual tokens relevant to the description of the anatomical structure, the breasts, abnormality, the tumor, and location of the tumor in the left or right breast. One or more relevant conceptual tokens may define a semantic structure describing the location of the abnormality with respect to the anatomical structure. These tokens can be identified using, for example, simple string matching techniques such as regular expressions. Conceptual tokens correspond to concepts from the vocabulary. Various metrics, also referred to as similarities or similarity measures, can be used to accept or eliminate candidate concepts from the vocabulary as, respectively, matching or not matching the conceptual tokens.

Optionally, relational tokens of the plurality of tokens may be used to determine relations between/among conceptual tokens and may be compared to relations between/among the concepts from the vocabulary. The relations between/among the concepts from the SNOMED CT vocabulary are defined in the SNOMED CT ontology. The relations between/among the concepts from the BI-RADS vocabulary are defined in the Breast Cancer Imaging Ontology (BCIO), which is based on BI-RADS. Again, various metrics can be used to accept or eliminate candidate relations between concepts from the vocabulary as matching the relational tokens.

In an embodiment, identifying the semantic structure describing the location of the abnormality with respect to the anatomical structure includes detecting whether the presence of an abnormality related to the location is negated or not. If the presence of the abnormality related to the location with respect to the anatomical structure is negated, the location of the abormality with respect to the anatomical structure is not identified by the analyzer, i.e., no semantic structure describing the location of the abnormality with respect to the anatomical structure is identified.

FIG. 3 illustrates indicating a location of a lesion number 1 on the breast diagram 31. Locations on the breast diagram 31 correspond to locations in the vocabulary for annotating the breast diagram 31. The breast diagram 31 is annotated by the mapper U30 based on the identified semantic structure describing the location of the abnormality with respect to the anatomical structure. The location of a speculated mass in the right periareolar region, slightly lateral and central to the nipple, is extracted from the exemplary report shown in FIG. 2.

FIG. 3 further illustrates the additional information 32, 33 about the identified abnormality number 1, extracted by the extractor U40 of the system SYS on the basis of the identified semantic structure. The additional information 32 is unstructured and shows a text highlighted in the report. The additional information 33 is structured and comprises entries in the fields named identifier, type, laterality and location of a record of the additional information. The field named depth of this record is empty.

In an embodiment, the extractor U40 of the system SYS comprises:

A candidate selection module for extracting a list of phrases which are potentially relevant for the user from the text. This module has access to a piece of domain knowledge, e.g., an ontology, to determine what are relevant terms in the current context. For instance, in the breast cancer domain one can use the list of BI-RADS terms as a source vocabulary that models the relevant terms. Optionally, the user may define or extend the vocabulary.

A phrase sense disambiguation module deciding whether a given candidate phrase is used in the intended sense in its context in the original text. If the candidate phrase is used in the intended sense, it is accepted for further processing by the disambiguation module, otherwise it is rejected.

A phrase expansion module for expanding candidate phrases by searching for informative adjectives, adverbs, etc., in the syntactic neighborhood of the phrase.

A negation detection module for checking if a candidate phrase is negated in its context in the report.

A co-reference module for checking whether a candidate phrase refers to an earlier discussed item or not.

A grouping module for checking whether any two or more candidate phrases describe the same entity, by mapping said candidate phrases into metadata comprised in a background ontology as such in BI-RADS. The grouping module compares the metadata of the candidate phrases and concludes that the first and second phrases refer to the same entity when they correspond to the same metadata.

For example, a report may comprise following two sentences: (i) "There is a smooth focally enhancing mass measuring 1×2 cm", and (ii) "There is no evidence for suspicious microcalcifications". The report is processed by the system SYS. The tokenizer U10 outputs the following tokens (the pipeline character "|" separates the tokens): "|there|is|a|smooth|focally|enhancing|mass|measuring|1|×|2|cm|.|there|is|no|evidence|of|suspicious|microcalcifications|.|" After stemming the tokens comprising words, the tokens are: "|there|is|a|smooth|focal|enhanc|mass|measure|1|×|2|cm|.|there|is|no|evid|of|suspici|microcalcifi.|" The candidate selection module of the extraction module selects from these sentences the following two terms: "mass" and "microcalcif". The phrase sense disambiguation module decides that both words are used in the intended sense. The phrase expansion module expands the two words, based on the as follows: "|smooth|focal|enhance|mass|measure|1|×|2|cm|" and "|suspici|microcalcifi". The negation detection module finds that the second phrase appears in a negation phrase "there is no evidence of". Hence the second phrase is tagged by said negation detection module as being negated. The co-reference module detects that neither of the words refer to another term used previously. The findings of the extraction module U40 can visualized, e.g., by highlighting the identified phrase in the report or displaying a phrase "Smooth focally enhancing mass measuring 1×2 cm" in a separate text window.

Finally, the grouping module extracts additional metadata of the phrases by mapping them to a background ontology. For example, let "left breast lesion" be another phrase found by the extraction unit U40 in the report. The following metadata defined in BI-RADS are assigned to each phrase:

| phrases | metadata |
|---|---|
| left breast lesion | laterality: left, type: mass |
| smooth focally enhancing mass measuring 1 × 2 cm | type: mass, size: 1 × 2 cm, description: smooth focally enhancing |

The grouping module compares the metadata of the two phrases and concludes that the first and second phrases refer to the same entity: the mass. Consequently, the presentation module may be arranged to present one merged entry, instead of two separate ones: "Smooth focally enhancing mass measuring 1×2 cm in the left breast".

A person skilled in the art will understand that all or some of the modules used by the extraction unit U40 may be also implemented in and employed by the analysis unit U20.

A person skilled in the art will appreciate that the system of the invention may be a valuable tool for assisting a physician in many aspects of her/his job. Further, although the embodiments of the system are illustrated using medical applications of the system, non-medical applications of the system are also contemplated.

Those skilled in the art will further understand that other embodiments of the system SYS are also possible. It is possible, among other things, to redefine the units of the system and to redistribute their functions. Although the described embodiments apply to medical images, other applications of the system, not related to medical applications, are also possible.

The units of the system SYS may be implemented using a processor. Normally, their functions are performed under the control of a software program product. During execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 4:
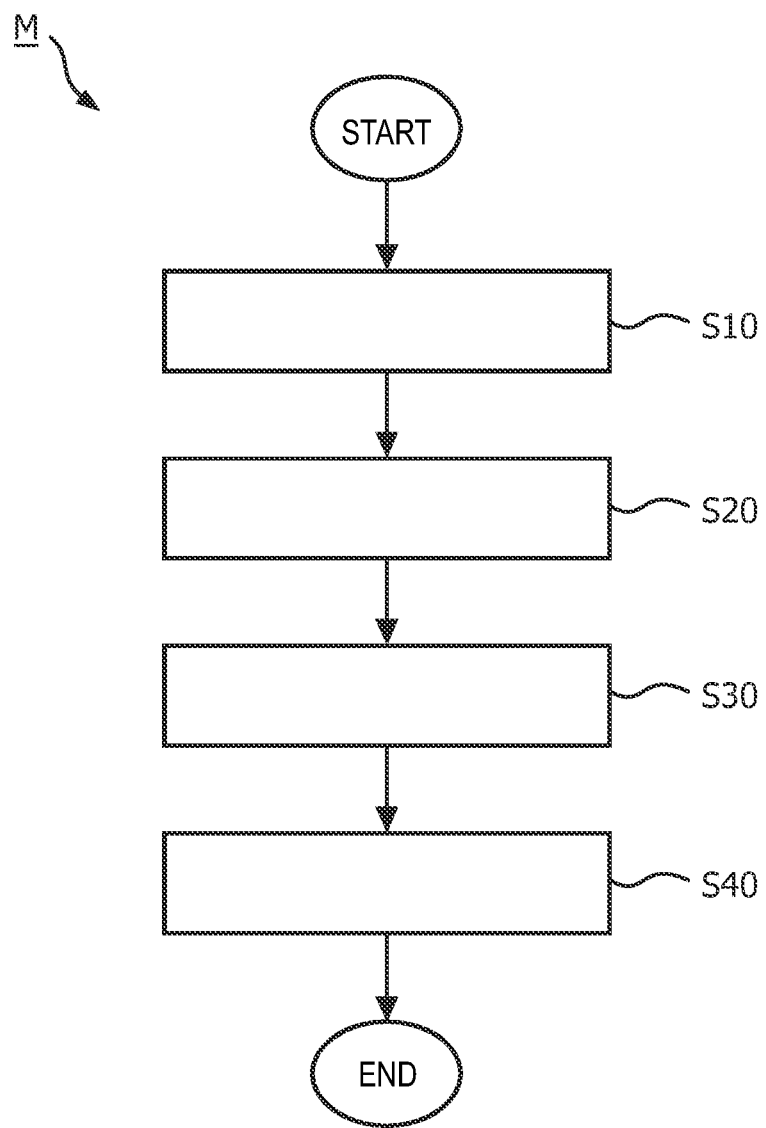
FIG. 4 schematically shows an exemplary flowchart of the method.

FIG. 4 shows an exemplary flowchart of an implementation of the method M of automatically extracting a location of an abnormality with respect to an anatomical structure from a report. The method begins with a tokenizing step S10 for tokenizing the report or a part of it, thereby producing a plurality of tokens. After the tokenizing step S10, the method M continues to an analyzing step S20 for identifying a semantic structure comprising identified tokens of the plurality of tokens, describing the location of the abnormality. After the analyzing step S20, the method M continues to a mapping step S30 for annotating a diagram representing the anatomical structure, based on the identified semantic structure describing the location of the abnormality with respect to the anatomical structure. After the mapping step S30, the method M continues to an extracting step S40 for extracting additional information about the identified abnormality, based on the identified semantic structure. After the extracting step S40, the method M terminates.

A person skilled in the art may change the order of some steps, add some optional steps (e.g. user interaction for inputting the abnormality to be searched in the report) or omit some non-mandatory steps, or perform some steps concurrently using threading models, multi-processor systems or multiple processes without departing from the concept as intended by the present invention. Optionally, two or more steps of the method M may be combined into one step. Optionally, a step of the method M may be split into a plurality of steps.

Figure 5:
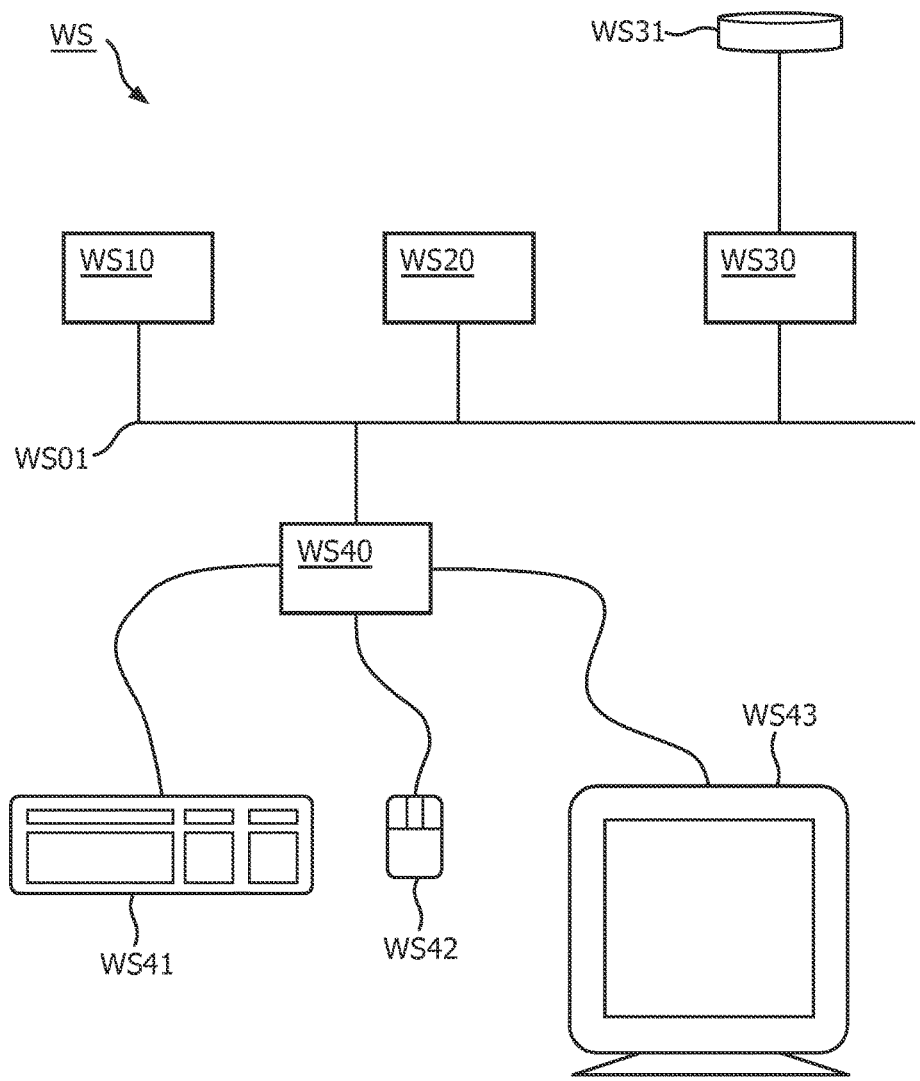
FIG. 5 schematically shows an exemplary embodiment of the workstation.

FIG. 5 schematically shows an exemplary embodiment of the workstation WS. The workstation comprises a system bus WS01. A processor WS 10, a memory WS20, a disk input/output (I/O) adapter WS30, and a user interface WS40 are operatively connected to the system bus WS01. A disk storage device WS31 is operatively coupled to the disk I/O adapter WS30. A keyboard WS41, a mouse WS42, and a display WS43 are operatively coupled to the user interface WS40. The system SYS of the invention, implemented as a computer program, is stored in the disk storage device WS31. The workstation WS00 is arranged to load the program and input data into memory WS20 and execute the program on the processor WS10. The user can input information to the workstation WS00, using the keyboard WS41 and/or the mouse WS42. The workstation is arranged to output information to the display device WS43 and/or to the disk WS31. A person skilled in the art will understand that there are numerous other embodiments of the workstation WS known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same record of hardware or software. The usage of the words first, second, third, etc., does not indicate any ordering. These words are to be interpreted as names.

The invention claimed is:

1. A system for automatically extracting a location of an abnormality with respect to an anatomical structure with a body comprising a plurality of anatomical structures from a report, the system comprising:
   a memory,
   a display, and
   a controller that controls:
      a tokenizer that tokenizes the report or a part of the report, thereby producing a plurality of tokens that are stored in the memory;
      an analyzer that identifies a semantic structure comprising at least one identified token of the plurality of token that describes the location of the abnormality with respect to the anatomical structure; and
      a mapper that indicates the location of the abnormality with respect to the anatomical structure on the display via a diagram representing the anatomical structure by annotating the diagram based on the identified semantic structure by adding a graphic visualization of the location of the abnormality on the diagram representing the anatomical structure;
   wherein the plurality of tokens includes at least one reference token that identifies a reference point in the anatomical structure;
   wherein the identified token describes the location of the abnormality relative to the reference point in the anatomical structure;
   wherein the diagram representing the anatomical structure includes a reference feature that corresponds to the reference point;
   wherein the mapper uses the location of the abnormality relative to the reference point in the anatomical structure to determine a corresponding abnormality location on the diagram relative to the reference feature; and
   wherein the mapper provides the graphic visualization of the abnormality at the abnormality location on the diagram.

2. The system of claim 1, wherein identifying the semantic structure includes comparing conceptual tokens of the plurality of tokens to concepts of a plurality of concepts in order to determine the identified token.

3. The system of claim 2, wherein comparing conceptual tokens of the plurality of tokens to concepts of a plurality of concepts includes computing a conceptual similarity between the conceptual tokens and the concepts.

4. The system of claim 2, wherein identifying the semantic structure further includes comparing relational tokens, describing relations between/among the conceptual tokens, to concept relations between/among the concepts of the plurality of concepts, in order to determine relations between/among the identified conceptual tokens.

5. The system of claim 2, wherein comparing the relational tokens to the concept relations between/among the concepts of the plurality of concepts includes computing a relational similarity between the relational tokens and the concept relations.

6. The system of claim 1, further comprising an extractor that extracts additional information about the identified abnormality, based on the identified semantic structure, the additional information comprising a size or palpability of the abnormality; wherein the graphic visualization is indicative of the size or palpability.

7. The system of claim 1, wherein the anatomical structure is a breast or axilla.

8. A workstation comprising the system of any one of the previous claims.

9. A method of automatically extracting a location of an abnormality with respect to an anatomical structure within a body comprising a plurality of anatomical structures from a report by a computer processor, the method comprising:
   tokenizing the report or a part of the report, thereby producing a plurality of tokens;
   identifying a semantic structure comprising at least one identified token of the plurality of tokens that describes the location of the abnormality; and
   indicating the location of the abnormality with respect to the anatomical structure on a diagram representing the anatomical structure by annotating the diagram based on the identified semantic structure by adding a graphic visualization of the location of the abnormality on the diagram representing the anatomical structure;
   wherein the plurality of tokens includes at least one reference token that identifies a reference point in the anatomical structure;
   wherein the identified token describes the location of the abnormality relative to the reference point in the anatomical structure;
   wherein the diagram representing the anatomical structure includes a reference feature that corresponds to the reference point;

wherein the mapper uses the location of the abnormality relative to the reference point in the anatomical structure to determine a corresponding abnormality location on the diagram relative to the reference feature; and wherein the mapper provides the graphic visualization of the abnormality at the abnormality location on the diagram.

10. A method as claimed in claim 9, wherein identifying the semantic structure includes comparing conceptual tokens of the plurality of tokens to concepts of a plurality of concepts in order to determine the identified token.

11. A method as claimed in claim 10, wherein identifying the semantic structure further includes comparing relational tokens, describing relations between/among the conceptual tokens, to concept relations between/among the concepts of the plurality of concepts in order to determine relations between/among the identified conceptual tokens.

12. The method of claim 10, wherein comparing conceptual tokens of the plurality of tokens to concepts of a plurality of concepts includes computing a conceptual similarity between the conceptual tokens and the concepts.

13. A method as claimed in claim 9, further comprising extracting additional information about the identified abnormality, based on the identified semantic structure, the additional information comprising a size or palpability of the abnormality; wherein the graphic visualization is indicative of the size or palpability.

14. A non-transitory computer readable medium that includes a program that, when executed by a processing system, causes the system to automatically extract a location of an abnormality with respect to an anatomical structure within a body comprising a plurality of anatomical structures from a report by:

tokenizing the report or a part of the report, whereby producing a plurality of tokens;

identifying a semantic structure comprising at least one identified token of the plurality of tokens that describes the location of the abnormality; and indicating the location of the abnormality with respect to the anatomical structure on a diagram representing the anatomical structure by annotating the diagram based on the identified semantic structure by adding a graphic visualization of the location of the abnormality on the diagram representing the anatomical structure;

wherein the plurality of tokens includes at least one reference token that identifies a reference point in the anatomical structure;

wherein the identified token describes the location of the abnormality relative to the reference point in the anatomical structure;

wherein the diagram representing the anatomical structure includes a reference feature that corresponds to the reference point;

wherein the mapper uses the location of the abnormality relative to the reference point in the anatomical structure to determine a corresponding abnormality location on the diagram relative to the reference feature; and wherein the mapper provides the graphic visualization of the abnormality at the abnormality location on the diagram.

15. The medium of claim 14, wherein the program causes the system to identify the semantic structure by comparing conceptual tokens of the plurality of tokens to concepts of a plurality of concepts in order to determine the identified token.

16. The medium of claim 15, wherein the program causes the system to compare conceptual tokens of the plurality of tokens to concepts of a plurality of concepts includes computing a conceptual similarity between the conceptual tokens and the concepts.

17. The medium of claim 15, wherein the program causes the system to identify the semantic structure further by comparing relational tokens, describing relations between/among the conceptual tokens, to concept relations between/among the concepts of the plurality of concepts, in order to determine relations between/among the identified conceptual tokens.

18. The medium of claim 15, wherein the program causes the system to compare the relational tokens to the concept relations between/among the concepts of the plurality of concepts by computing a relational similarity between the relational tokens and the concept relations.

19. The medium of claim 14, wherein the program causes the system to extract additional information about the identified abnormality, based on the identified semantic structure, the additional information comprising a size or palpability of the abnormality; wherein the graphic visualization is indicative of the size or palpability.

20. The medium of claim 14, wherein the program causes the system to extract additional information about the identified abnormality, based on the identified semantic structure, the additional information comprising a size or palpability of the abnormality.

* * * * *